United States Patent [19]
Dumoulin et al.

[11] Patent Number: 5,479,925
[45] Date of Patent: Jan. 2, 1996

[54] MAGNETIC RESONANCE (MR) ANGIOGRAPHY IN A LOW-FIELD IMAGING MAGNET

[75] Inventors: Charles L. Dumoulin, Ballston Lake; Robert D. Darrow, Scotia, both of N.Y.

[73] Assignee: General Electric Company, Schenectady, N.Y.

[21] Appl. No.: 264,283

[22] Filed: Jun. 23, 1994

[51] Int. Cl.$^6$ .................................................. A61B 5/055
[52] U.S. Cl. .................................... 128/653.3; 128/653.4; 324/306; 324/309
[58] Field of Search ............................. 128/653.2–653.4; 324/306, 309, 319

[56] References Cited

U.S. PATENT DOCUMENTS 5,154,603  10/1992  Sepponen ............................. 128/653.2
5,271,399  12/1993  Listerud et al. ..................... 128/653.3

*Primary Examiner*—Ruth S. Smith
*Attorney, Agent, or Firm*—Lawrence P. Zale; Marvin Snyder

[57] ABSTRACT

A magnetic resonance (MR) active invasive device system employs a small, high-field polarizing magnet, and a large low-field magnetic resonance (MR) imaging magnet for the purpose of generating MR angiograms of selected blood vessels. A subject is positioned in a large low-field MR imaging magnet. A catheter in inserted into the patient at or near the root of a vessel tree desired to be imaged. A fluid, intended to be used as a contrast agent is first passed through the small high-field polarizing magnet, causing a great deal of net longitudinal magnetization to be produced in the fluid. The fluid is then introduced into the subject through the catheter. Radiofrequency (RF) pulses and magnetic field gradients are then applied to the patient as in conventional MR imaging. Since the fluid has a larger longitudinal magnetization, before the MR imaging sequence, the fluid produces a much larger MR response signal than other tissue resulting in the vessel tree being imaged with excellent contrast.

4 Claims, 3 Drawing Sheets

MAGNETIC RESONANCE (MR) ANGIOGRAPHY IN A LOW-FIELD IMAGING MAGNET

CROSS REFERENCES TO RELATED APPLICATIONS

This application is related to U.S. patent applications Ser. No. 08/264,281 filed Jun. 23, 1994 "METHOD FOR BLOOD FLOW ACCELERATION AND VELOCITY MEASUREMENT USING MR CATHETERS" by Darrow, Dumoulin; Ser. No. 08/264,282 filed Jun. 23, 1994 "MAGNETIC RESONANCE (MR) ANGIOGRAPHY USING A FARADAY CATHETER" by C. Dumoulin, S. Souza; "TRACKING SYSTEM AND PULSE SEQUENCES TO MONITOR THE POSITION AND ORIENTATION OF A DEVICE USING MAGNETIC RESONANCE" Ser. No. 07/861,718 by C. Dumoulin, S. Souza and R. Darrow; "TRACKING SYSTEM TO MONITOR THE POSITION AND ORIENTATION OF A DEVICE USING MAGNETIC RESONANCE DETECTION OF A SAMPLE CONTAINED WITHIN THE DEVICE" Ser. No. 07/861,662 by C. Dumoulin, S. Souza and R. Darrow, filed on Apr. 1, 1992; and "TRACKING SYSTEM TO MONITOR THE POSITION AND ORIENTATION OF A DEVICE USING MULTIPLEXED MAGNETIC RESONANCE DETECTION" Ser. No. 07/861,690 by C. Dumoulin, S. Souza and R. Darrow; all assigned to the present assignee, and all incorporated by reference.

BACKGROUND OF THE INVENTION

1. Field of the Invention

The present invention relates to medical imaging of blood vessels, and more particularly concerns the use of magnetic resonance to obtain such imaging.

2. Description of Related Art

Angiography, or the imaging of vascular structures, is very useful in diagnostic and therapeutic medical procedures. In X-ray angiography, a bolus of x-ray opaque liquid is placed into the vessel of interest through an invasive device placed into the vessel. While the bolus is within the vessel, a series of X-ray images is obtained which highlight the X-ray absorbing liquid.

X-ray angiography carries several significant risks to the patient. For example, the X-ray opaque liquid can cause discomfort and adverse reactions within the patient. While conventional X-ray fluoroscopes are designed to minimize X-ray dosage, some procedures can be very long and the accumulated X-ray dose to the subject can become significant. The long term exposure of the attending medical staff is of even greater concern since they participate in these procedures regularly. Consequently, it is desirable to reduce or eliminate the X-ray dose during these procedures.

X-ray angiography, typically produces a single two-dimensional image. Information concerning the depth of an object within the field-of-view is not available to the operator. It is often desirable to obtain this information during diagnostic and therapeutic procedures.

Magnetic resonance (MR) imaging procedures for the imaging of vascular structures have recently become available. MR angiography is performed with a variety of methods, all of which rely on one of two basic phenomena. The first phenomena arises from changes in longitudinal spin magnetization as blood moves from one region of the patient to another. Methods that make use of this phenomenon have become known as "in-flow" or "time-of-flight" methods. A commonly used time-of-flight method is three-dimensional time-of-flight angiography. With this method, a region of interest is imaged with a relatively short repetition time, TR, and a relatively strong excitation radio-frequency (RF) pulse. This causes the MR spins within the field-of-view to become saturated and give weak MR response signals. Blood flowing into the field-of-view, however, enters in a fully relaxed state. Consequently, this blood gives a relatively strong MR response signal, until it too becomes saturated. Because of the nature of blood vessel detection with time-of-flight methods, the stationary tissue surrounding the vessel cannot be completely suppressed. In addition, slowly moving blood, and blood that has been in the imaged volume for too long, becomes saturated and is poorly imaged.

A second type of MR angiography is based on the induction of phase shifts in transverse spin magnetization. These phase shifts are directly proportional to velocity and are induced by flow-encoding magnetic field gradient pulses. Phase-sensitive MR angiography methods exploit these phase shifts to create images in which the pixel intensity is a function of blood velocity. While phase-sensitive MR angiography can easily detect slow flow in complicated vessel geometries, it will also detect any moving tissue within the field-of-view. Consequently, phase-sensitive MR angiograms of the heart have artifacts arising from the moving heart muscle and from the moving pools of blood in the heart chambers.

In conventional MR imaging, an inhomogeneity of the static magnetic field produced by the main magnet causes distortion in the image. Therefore a main magnet having homogeneity over a large region is desirable.

Also, the stronger the static magnetic field created by the main magnet, the better the signal to noise ratio with all other factors being equal. Typically, these main magnets have been constructed of a superconducting material requiring very low temperatures, and all related support apparatus. This can become very expensive.

There is also the problem of shielding a large high-field magnet. Entire shielding rooms have been constructed to reduce the effects of the magnetic field on nearby areas and equipment.

Currently, there is a need for a system for obtaining high quality angiography of a selected vessel without the risks of exposure to ionizing radiation and X-ray opaque contrast injections, and without the problems incurred with a large high-field main magnet.

SUMMARY OF THE INVENTION

A fluid is passed through a small high-field polarizing magnet before it is injected into a catheter inserted in a vessel of a patient. In order to achieve maximum polarization the fluid is made to reside in the polarizing field longer than several T1 periods. The polarized fluid is then rapidly injected into the patient. MR images are created of the polarized fluid with an MR system which comprises radio-frequency and magnetic field gradient coils and a less powerful static field imaging magnet. The overall system requires much less power to function than a conventional high-field imaging system, and employs a simpler, less expensive static imaging magnet which may be a resistive or permanent magnet instead of a superconducting magnet.

OBJECTS OF THE INVENTION

It is an object of the present invention to provide a system for imaging selected blood vessels using magnetic resonance without the need for a homogeneous high-field imaging magnet.

It is another object of the present invention to provide an MR angiography system which is simpler than prior art systems.

BRIEF DESCRIPTION OF THE DRAWINGS

The features of the invention believed to be novel are set forth with particularity in the appended claims. The invention itself, however, both as to organization and method of operation, together with further objects and advantages thereof, may be best understood by reference to the following description taken in conjunction with the accompanying drawing in which:

DETAILED DESCRIPTION OF THE INVENTION

Figure 1:
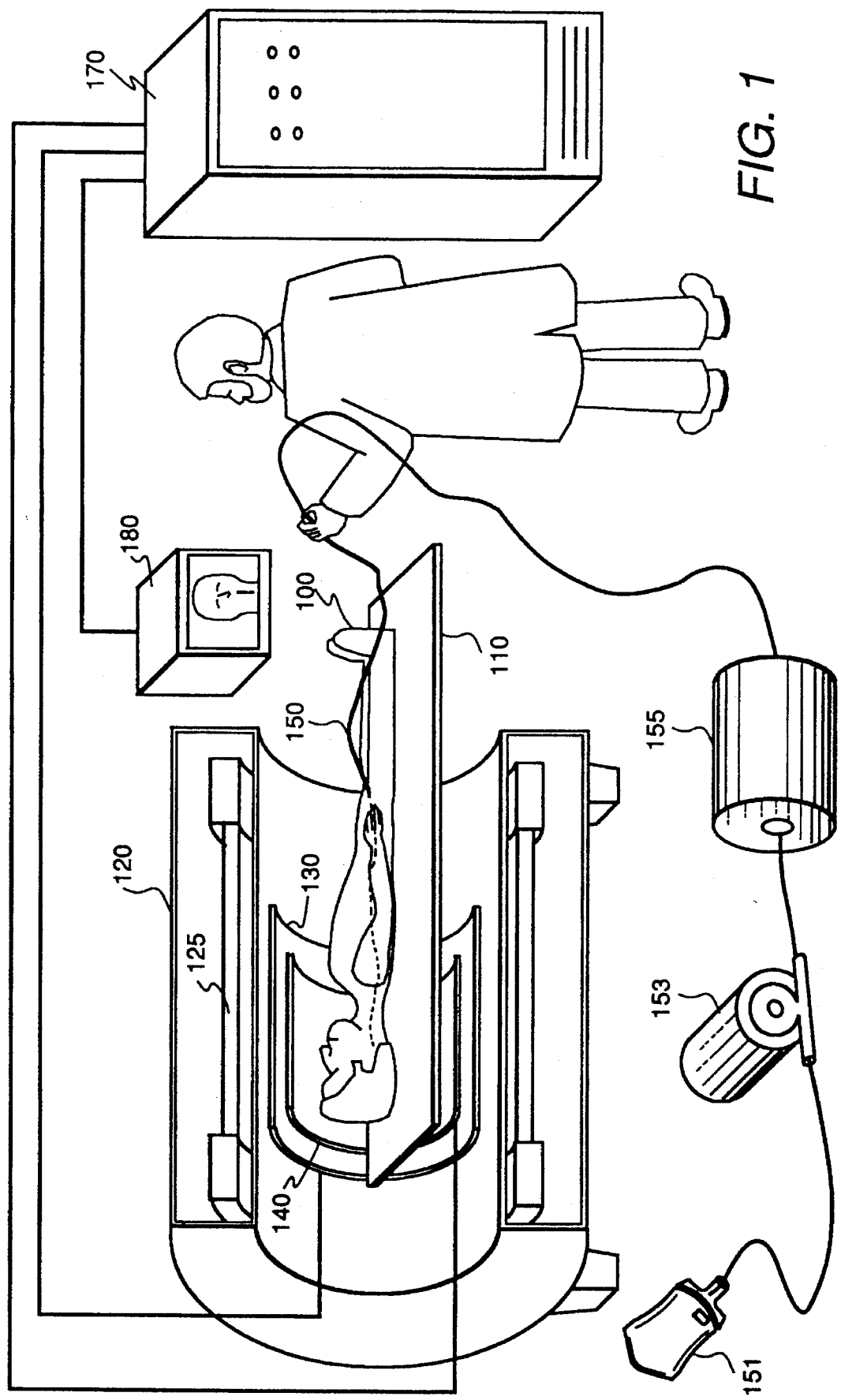
FIG. 1 is a perspective view of a first embodiment of the present invention in operation in which a vessel selective angiogram is being obtained from a subject.

In FIG. 1, a subject 100 is placed on a support table 110 and positioned in a homogeneous magnetic field generated by a magnet 125 encased in a magnet housing 120. In this embodiment, magnet 125 and magnet housing 120 have cylindrical symmetry and are shown sectioned in half to reveal the position of subject 100. A region of interest of subject 100 is located in the approximate center of the bore of magnet 125. Subject 100 is surrounded by a set of cylindrical magnetic field gradient coils 130 which create magnetic field gradients of predetermined strength at predetermined times according to predetermined MR pulse sequences, described later. Gradient coils 130 are capable of generating pulsed magnetic field gradients in three mutually orthogonal directions. At least one radio-frequency (RF) coil 140 (only one is shown in FIG. 1) also surrounds the region of interest of subject 100. In FIG. 1, RF coil 140 has a cylindrical shape with a diameter sufficient to encompass the entire subject. Other geometries, such as smaller cylinders specifically designed for imaging the head or an extremity, can be used in alternative embodiments. Non-cylindrical RF coils, such as surface coils, may also be used. Imaging electronics 170 drives RF coil 140 to radiate radio-frequency energy into subject 100 at predetermined times and with sufficient power at a predetermined frequency so as to nutate a population of nuclear magnetic spins, hereinafter referred to as 'spins', of subject 100 in a fashion well known to those skilled in the art. RF coil 140 can also act as a receiver, detecting the MR response signals which are stimulated by nutation, if desired.

The nutation of the spins causes them to resonate at the Larmor frequency. The Larmor frequency for each spin is directly proportional to the strength of the magnetic field experienced by the spin. This field strength is the sum of the static magnetic field generated by magnet 125 and the local field generated by Imaging electronics 170 driving magnetic field gradient coil 130.

Fluid in a fluid reservoir 151 is passed through a polarizing magnet 155 by a pump 153, if required.

Polarizing magnet 155 is a superconducting magnet operating with relatively poor homogeneity, but as high a field as possible. Designs in which the field strength approaches 15 Tesla or more should be possible. The magnet should be fully shielded to prevent stray magnetic fields from disturbing the surrounding environment. This shielding can be accomplished with an active cancellation coil surrounding the internal main coil, or it can be accomplished by creating a superconducting shield around the magnet coil. Since polarizing magnet 155 is not required to have a great deal of homogeneity, and because of its small size, the magnet should be considerably less expensive than existing MR imaging magnets.

The polarized fluid is then injected through catheter 150 into subject 100 where it is imaged using conventional MR imaging methods.

The fluid which is injected into the subject 100 through catheter 150 should have the highest amount of polarization possible once it reaches the vessels. Consequently, the polarizing field of polarizing magnet 155 should be high. Also, the fluid will have to be left in the polarizing field for a period of time greater than five times the T1 of the fluid to reach full magnetization. Once the fluid leaves polarizing magnet 155 it will begin to lose polarization with a half-life equal to its T1. Consequently, it is desirable to deliver the fluid to the patient as quickly as possible. This can be done by minimizing the length of the catheter and maximizing the flow velocity.

The fluid in fluid reservoir 151 should have a T1 chosen to be as long as possible to maximize the amount of polarization delivered into the vessels of the patient. Possible choices of fluid are:

1) physiological saline solution;

2) blood previously obtained from the patient;

3) whole blood or plasma from a donor; and 4) a blood substitute such as fluoridated hydrocarbons capable of carrying oxygen to tissue; and 5) blood recirculated from the patient.

The imaging system will have the same elements as a conventional MR imaging system, however, they will function differently. A static magnetic field from a main imaging magnet, shown as 125 in FIGS. 1, 3, should be extremely low (such as 0.1 Tesla) to prevent signals from "stationary" tissue and undesired blood pools contributing to the angiographic image. A small high-field polarization magnet 155 and a large low-field main magnet, instead of a large high-field main magnet will reduce the cost of the system greatly.

Figure 3:
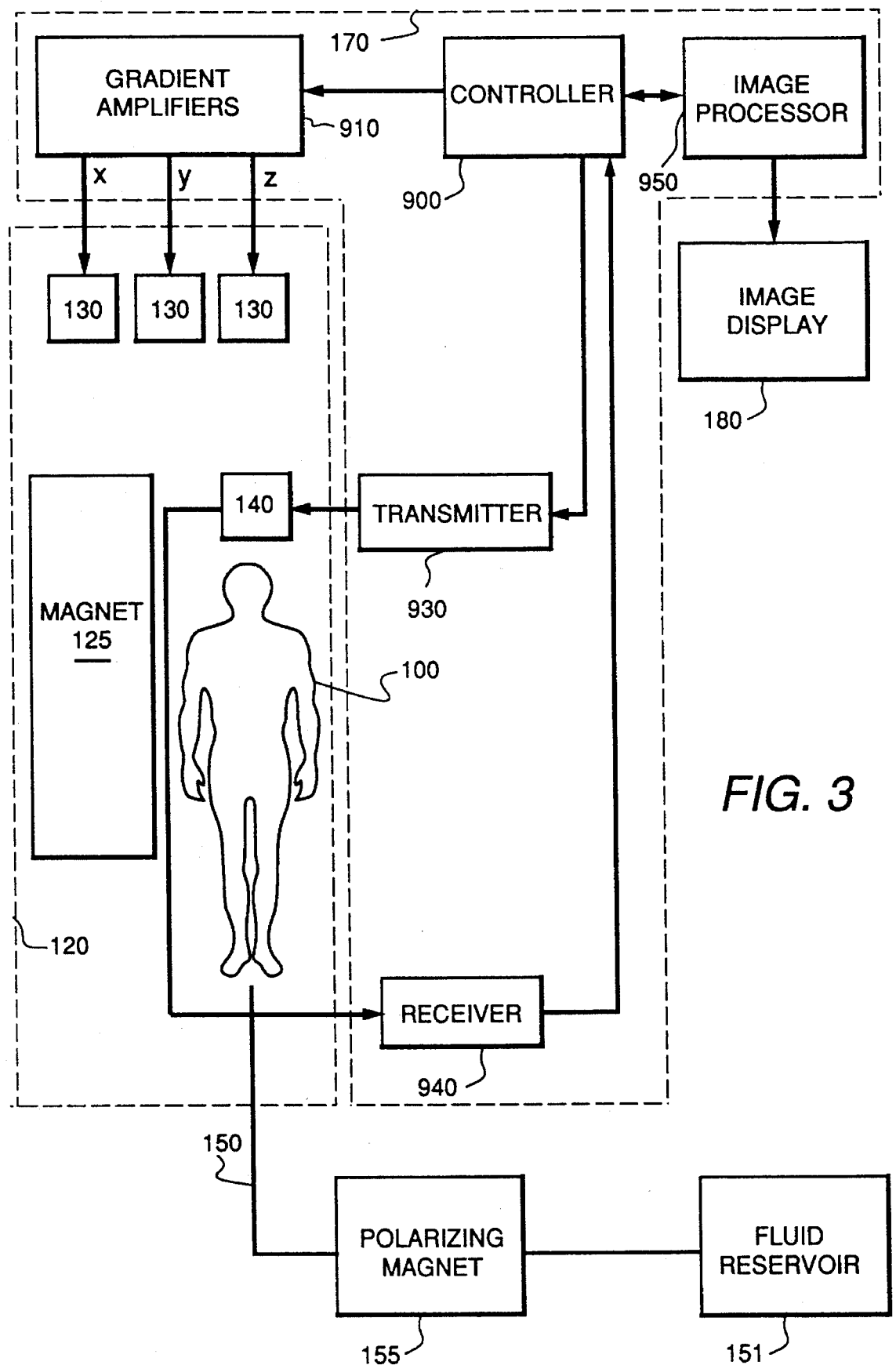
FIG. 3 is a block diagram of a vessel selective MR imaging system suitable for MR angiography according to the present invention.

RF transmitter 930 and RF receiver 940 of the MR system shown in FIG. 3 would be modified to be compatible with the low-field magnet to resonate at a Larmor frequency corresponding to the strength of magnet 125 (e.g., 4.26 MHz in a 0.1T magnetic field).

In an alternate embodiment, imaging magnet 125 could be an electromagnet which is driven by an amplifier similar to amplifier 910. Such a system shall be able to create a pulsed homogeneous field of 30 Gauss (Larmor frequency=128 KHz). Shielded gradient coil designs may be unnecessary with the present invention employing of a low-field main magnet 125 (although one may still want them to prevent interference with nearby equipment).

RF transmitter 930, and RF coil 140 of the present invention perform the same functions as an RF subsystem of a conventional MR imaging device. Because the Larmor frequency is very low, however, RF coil designs having resonant frequencies comparable to the Larmor frequency will be required. At these lower frequencies, very little RF transmit power will be required, being a further advantage of the present invention.

A controller 900 provides control signals to magnetic field gradient amplifiers 910. These amplifiers drive magnetic field gradient coils 130 situated within the magnet enclosure 120. Gradient coils 130 are capable of generating magnetic field gradients in three mutually orthogonal directions.

Controller 900 generates signals which are supplied to transmitter 930 to generate RF pulses at one or more predetermined frequencies and with suitable power to nutate selected spins within RF coil 140 situated within the bore of magnet 125.

MR response signals are sensed by RF coil 140 connected to receiver 940. Since the fluid from fluid reservoir 151 has passed through polarizing magnet 155, it acquires a significantly larger longitudinal magnetization, $M_L$, than 'spins' which are only subjected to low-field magnet 125. Consequently, when nutated by the RF pulses, 'spins' which have passed through polarizing magnet 155 exhibit larger transverse magnetization, $M_T$, and consequently produce a much larger MR response signal. Receiver 940 processes the MR response signals by amplifying, demodulating, filtering and digitizing. Controller 900 also collects the signals from receiver 940 and propagates them to a image processor 950 where they are processed. Image processor 950 applies a Fourier transformation to the signals received from controller 900 to create an MR image. The image created by image processor 950 is displayed on an image display 180.

Compared to conventional imaging, the MR response signal of 'spins' which did not pass through polarizing magnet 155 experience a 0.1T magnetic field, 15 times lower than that experienced by a conventional 1.5T MR imaging system. A 10T polarizing magnet 155 produces 6.67 times more polarization than a conventional 1.5T main magnet for fluid 151 which passes through polarization magnet 155. Therefore, the MR signal difference, or contrast, between polarized and non-polarized 'spins' would be on the order of 100 times.

Figure 2:
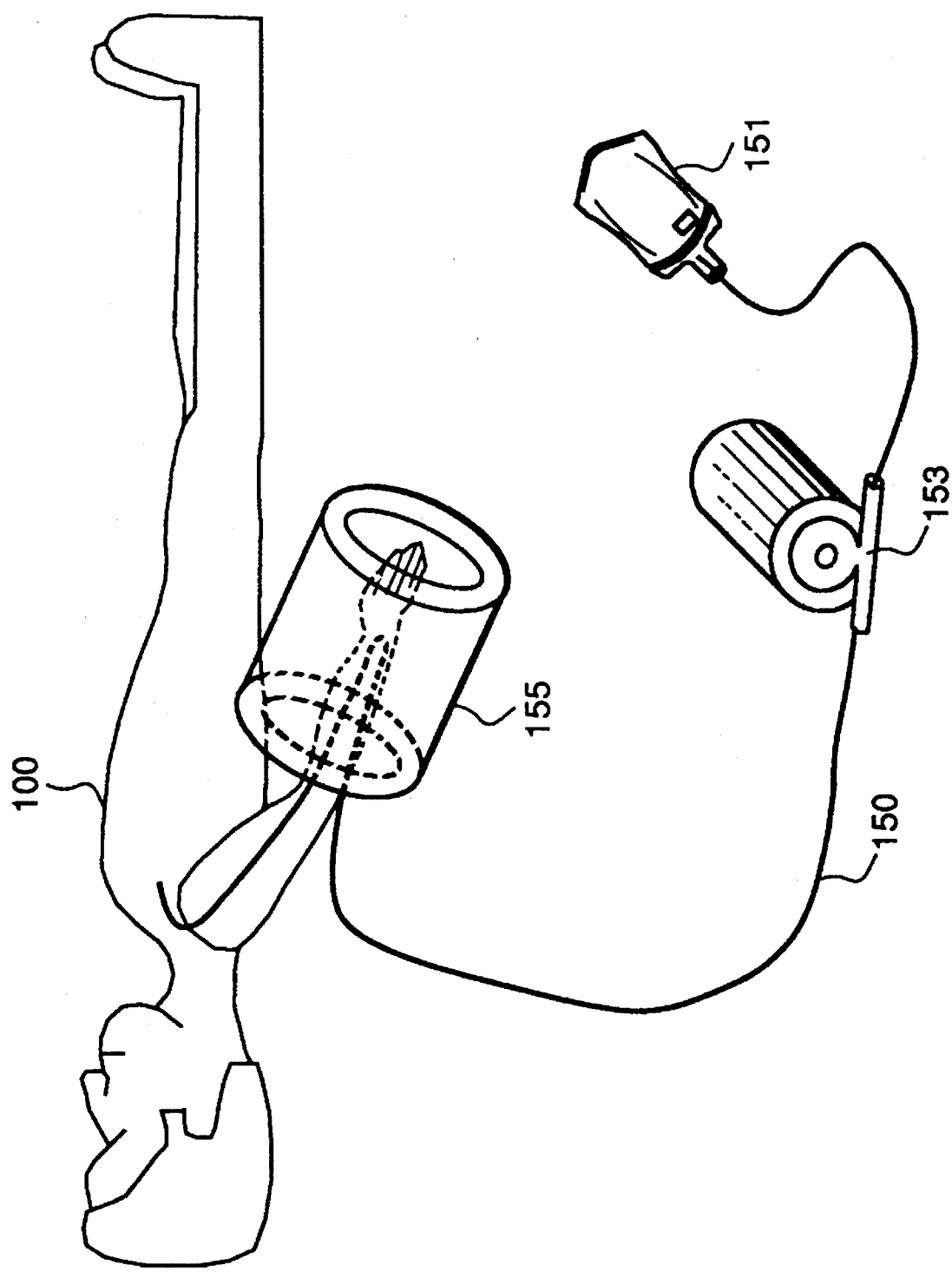
FIG. 2 is a perspective view of a second embodiment of the present invention in operation in which a vessel selective angiogram is being obtained from a subject.

Another embodiment of the invention, shown in FIG. 2 is to place part of subject 100 in polarizing magnet 155 to maximize the polarization in fluid 151 delivered to the vascular tree, by pump 153, if necessary. Here catheter 150 is inserted into the arm of the subject 100. Catheter 150 and subject's arm are then placed into polarizing magnet 155. The distance that the polarized fluid must travel to the vessel tree (and hence the time during which polarization can be lost) is greatly reduced. Conventional MR Imaging pulse sequence employed in creating angiograms are compatible with the present invention; consequently, both time-of-flight and phase-sensitive methods will work well.

The MR system outlined in FIG. 3 may also be used for the generation of conventional MR images in a manner well known to those skilled in the art. Received MR response signals are detected with either the same RF coil used by the transmitter or a surface coil independent of the coil driven by the transmitter.

While several presently preferred embodiments of the novel MR vascular imaging system have been described in detail herein, many modifications and variations will now become apparent to those skilled in the art. It is, therefore, to be understood that the appended claims are intended to cover all such modifications and variations as fall within the true spirit of the invention.

What is claimed is:

1. A nuclear magnetic resonance (NMR) imaging system for obtaining vessel-selective NMR angiographic images from a subject comprising:

a) a nuclear magnetic resonance (NMR) active fluid having nuclei capable of producing an NMR signal;

b) a low-field imaging magnet for applying a substantially uniform magnetic field over said subject;

c) a high-field polarizing magnet for polarizing the nuclei of the NMR active fluid;

d) a catheter for routing the polarized NMR active fluid from the high-field polarizing magnet into a selected vessel of said subject within the low-field imaging magnet;

e) an RF transmitter means for transmitting RF energy into said subject of a selected duration, amplitude and frequency to directly cause nutation of the polarized NMR active fluid within said subject;

f) a gradient means for varying the amplitude of the magnetic field in at least one spatial dimension over time;

g) an RF receive coil for detecting a set of NMR response signals from the NMR active fluid within said subject;

a) a receiver means coupled to the RF receive coil for receiving the detected NMR response signals from the NMR active fluid in the selected vessel;

i) an image processor means for creating an angiographic image from the detected NMR response signals;

j) a controller means connected to the RF transmitter means, the receiver means, the image processor means and the gradient means, for activating the RF transmitter means, the receiver means, the image processor means and the gradient means each according to a predetermined NMR pulse sequence; and k) a display means connected to the image processor means for displaying the angiographic image of the selected vessel to an operator.

2. A nuclear magnetic resonance (NMR) imaging system for obtaining NMR angiographic images of a subject having a circulating NMR active fluid having nuclei capable of nuclear magnetic resonance comprising:

a) a low-field imaging magnet for applying a substantially uniform magnetic field over said subject;

b) a high-field polarizing magnet having a magnetic field strength substantially greater than that of the low-field imaging magnet, for receiving a portion of said subject and for polarizing nuclei of the NMR active fluid circulating through the portion of said subject within the polarizing magnet;

c) an RF transmitter means for transmitting RF energy into a region of said subject desired to be imaged, without transmitting RF cherry into the portion of said subject received by the high-field magnet, the RF transmitter means transmitting RF energy of a selected duration, amplitude and frequency to directly cause nutation of the polarized nuclei of the NMR active fluid;

d) a gradient means for varying the amplitude of the magnetic field in at least one spatial dimension over time;

e) an RF receive coil for detecting a set of NMR response signals from the NMR active fluid within the desired imaging region of said subject;

f) a receiver means coupled to the RF receive coil for receiving the detected NMR response signals;

g) an image processor means for creating an angiographic image from the detected NMR response signals;

h) a controller means connected to the RF transmitter means, the receiver means, the image processor means end the gradient means, for activating the RF transmitter means, the receiver means, the image processor means end the gradient means each according to a predetermined NMR pulse sequence; and i) a display means connected to the image processor means for displaying the angiographic image to an operator.

3. A method of obtaining nuclear magnetic resonance (NMR) angiographic images of selected vessels of a subject comprising:

a) applying a substantially homogeneous magnetic field over said subject;

b) passing an NMR active fluid having nuclei capable of nuclear magnetic resonance, through a high-field polarizing magnet substantially in the absence of radiofrequency (RF) excitation energy, causing polarization of the nuclei of the NMR active fluid;

c) routing the NMR active fluid from the polarizing magnet and into a selected vessel of said subject;

d) transmitting RF energy into said subject of a selected duration, amplitude and frequency to directly cause nutation of the polarized nuclei of the NMR active fluid;

e) varying the amplitude of the magnetic field in at least one spatial dimension over time;

f) detecting a set of NMR response signals from the nuclei of the NMR active fluid within said subject;

g) receiving the detected NMR response signals;

h) processing the detected the detected NMR response signal to create an angiographic image; and i) displaying the processed angiographic image to an operator.

4. A method for obtaining magnetic resonance (NMR) angiographic images from a subject having circulating NMR active fluid having nuclei capable of nuclear magnetic resonance comprising the steps of:

a) applying a substantially homogeneous magnetic field over said subject;

b) positioning a portion of said subject within a high-field polarizing magnet in the absence of applied radiofrequency (RF) excitation energy, causing polarization of the nuclei of the NMR active fluid as it circulates through the portion of said subject within the polarizing magnet;

c) transmitting RF energy into said subject of a selected duration, amplitude and frequency to directly cause nutation of the polarized nuclei of the NMR active fluid within a region of said subject desired to be imaged;

d) varying the amplitude of the magnetic field in at least one spatial dimension over time;

e) detecting a set of NMR response signals from the nuclei of the NMR active fluid within the desired imaging region of said subject;

f) receiving the detected NMR response signals;

g) processing the detected NMR response signals to create an angiographic image; and h) displaying the processed angiographic image to an operator.

\* \* \* \* \*